United States Patent [19]

Lash et al.

[11] Patent Number: 4,770,187
[45] Date of Patent: Sep. 13, 1988

[54] SURGICAL ASPIRATOR AND MONITOR

[75] Inventors: Robert Lash, Foser City, Calif.; Gregory Hatfield, Minneapolis, Minn.

[73] Assignee: MD Engineering, Hayward, Calif.

[21] Appl. No.: 66,991

[22] Filed: Jun. 29, 1987

[51] Int. Cl.⁴ ............................................. A61B 5/00
[52] U.S. Cl. .................... 128/760; 604/318; 604/404; 324/61 P; 324/65 P
[58] Field of Search ............... 128/749, 751, 752, 760, 128/763, 766, 768; 604/317, 318, 319, 320, 404; 324/61 R, 61 P, 65 P

[56] References Cited

U.S. PATENT DOCUMENTS 3,182,252  5/1965  Van den Berg ................... 324/65 P
4,510,436  4/1985  Raymond .......................... 324/61 P

FOREIGN PATENT DOCUMENTS 164924  9/1964  U.S.S.R. ............................. 604/318

Primary Examiner—Edward M. Coven
Assistant Examiner—Randy Citrin
Attorney, Agent, or Firm—Harris Zimmerman; Howard Cohen

[57] ABSTRACT

An apparatus for surgical aspiration and monitoring of the aspirated fluids includes a sealable aspiration bottle supported by an electronic weighing scale on a base stand. The bottle includes tubing connectors joined to a negative gauge pressure source and to an aspirating surgical instrument. A pair of electrodes extend into the bottle and are connected to an electronic circuit which measures the impedance of the fluid/tissue aspirate in the bottle. A microprocessor receives the impedance and net weight data of the aspirate, determines the relative amounts and net weights of fluid and tissue in the aspirate, and displays this information on a visual display.

16 Claims, 3 Drawing Sheets

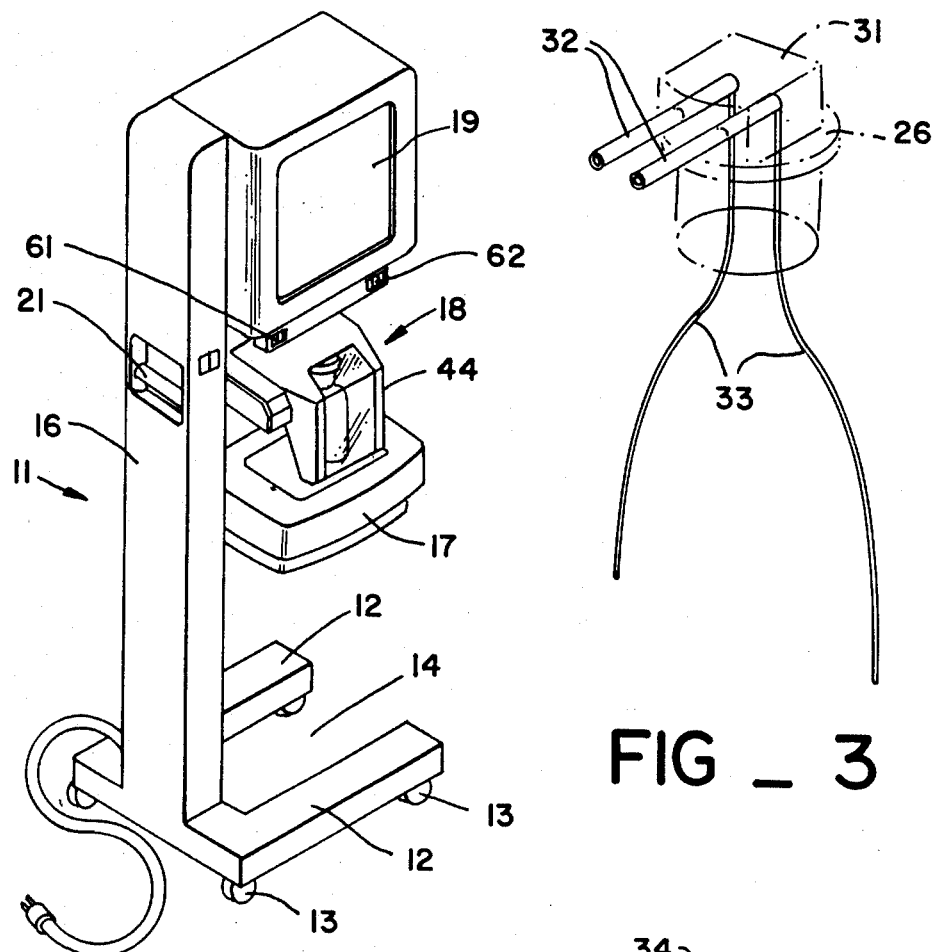
FIG _ 1
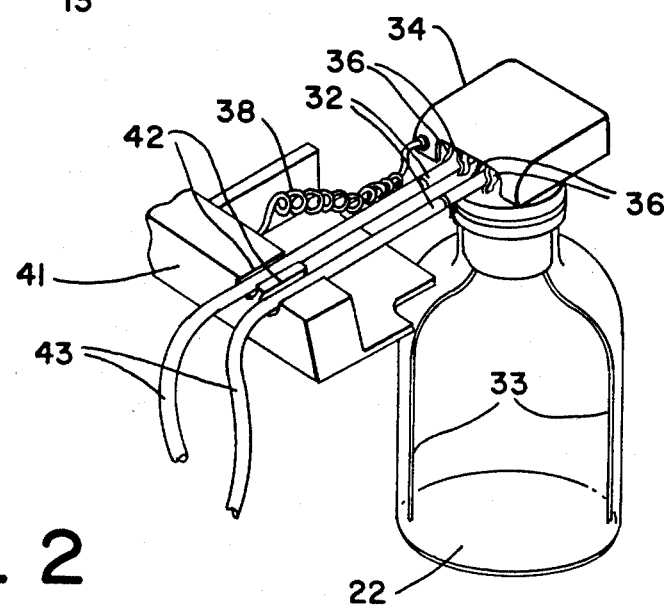
FIG _ 3
FIG _ 2

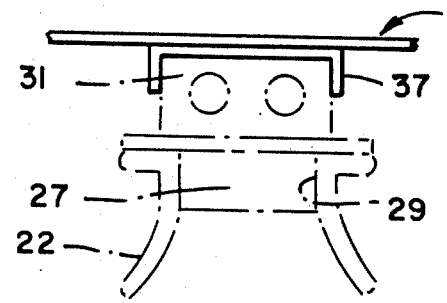
FIG _ 5
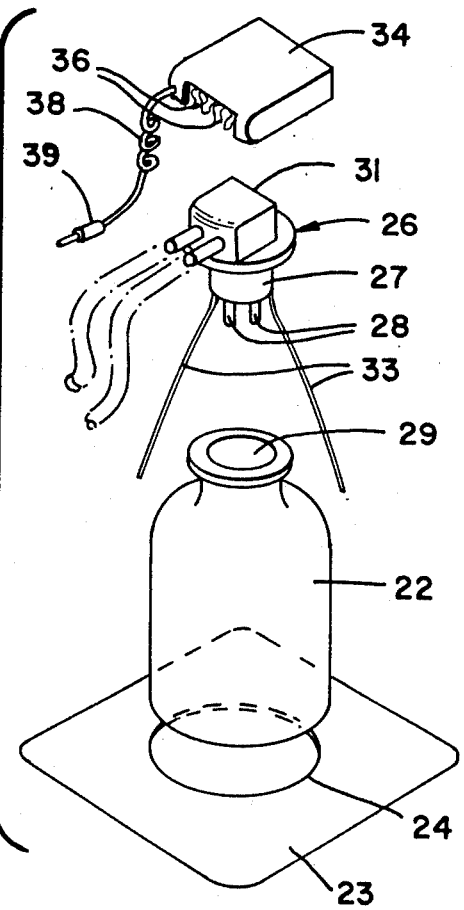
FIG _ 4
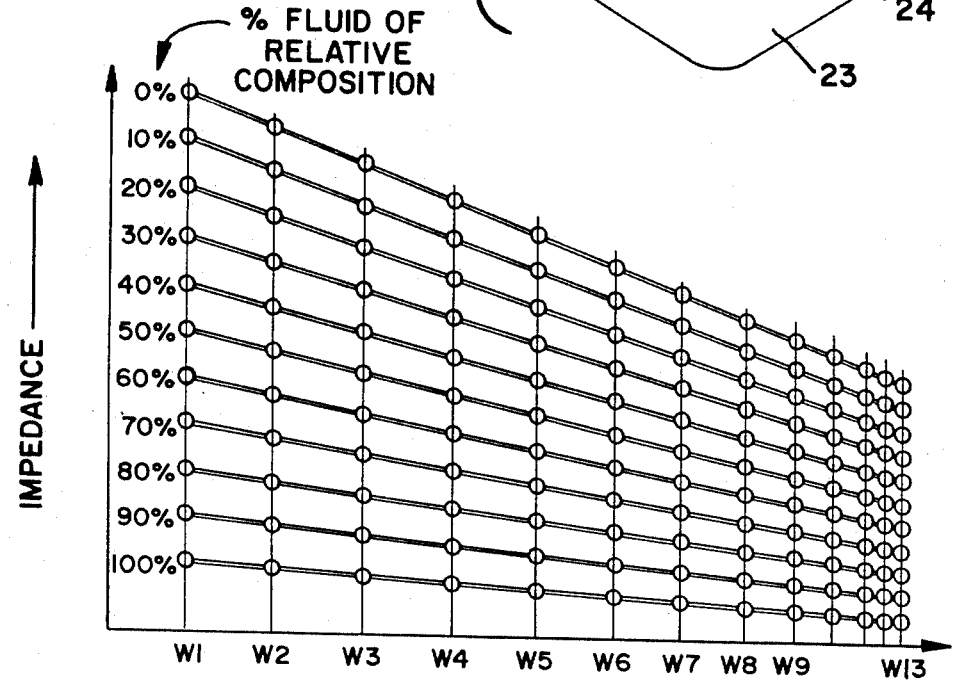
FIG _ 6

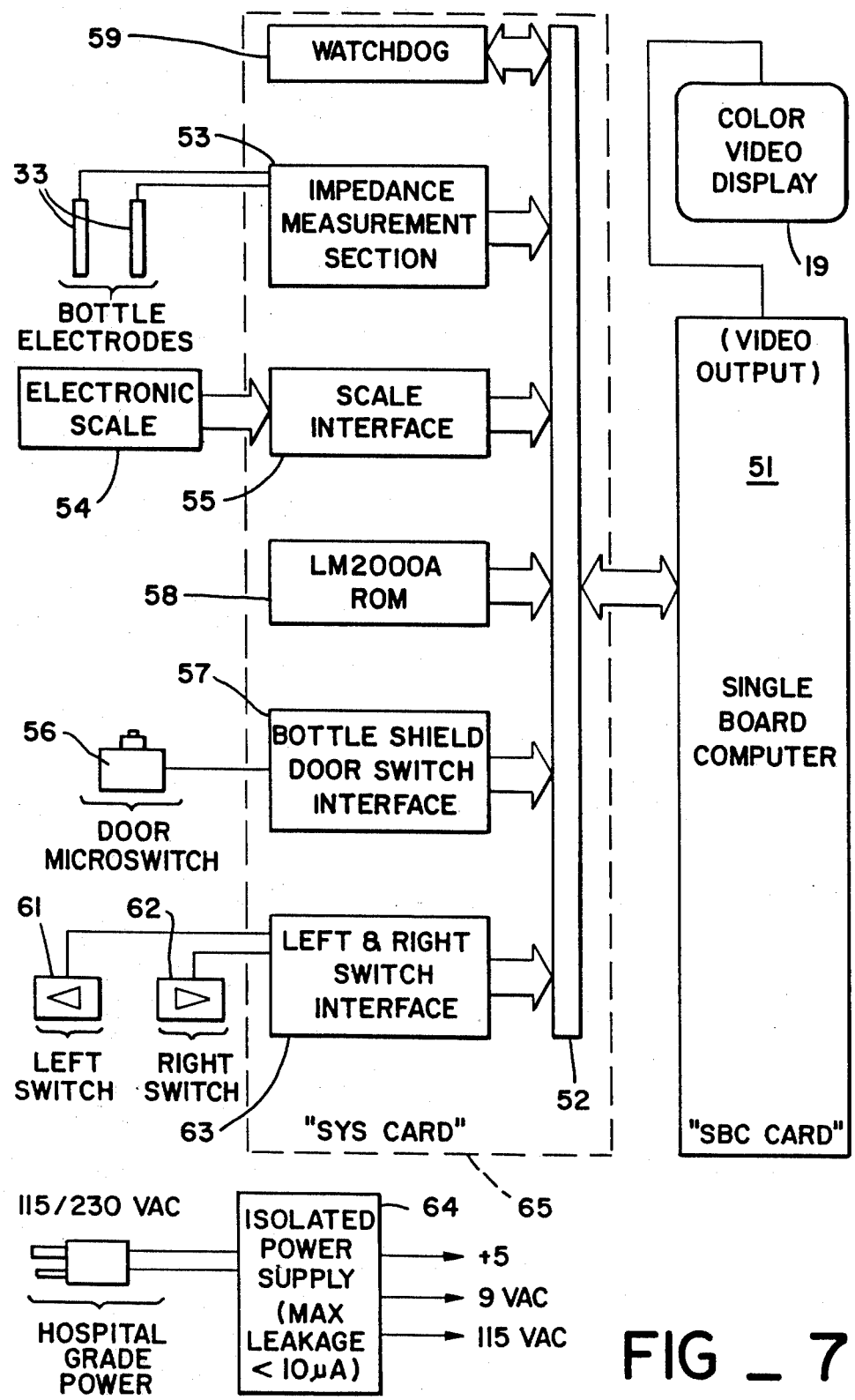
FIG_7

SURGICAL ASPIRATOR AND MONITOR

BACKGROUND OF THE INVENTION

In modern medical practice, virtually all surgical procedures require some form of aspiration. Surgical aspiration is generally required to remove fluids from the surgical site to maintain unobstructed visualization of the field. More recently, many surgical instruments and microsurgical devices employ aspiration to draw fluids and tissue into mechanically driven cutters which greatly increase the speed of tissue removal while reducing the effort required by the surgeon. Also, some surgical procedures, such as lipectomy and the like, rely solely on aspiration to remove certain tissue and deposit.

Generally speaking, the aspirate from most of these devices and procedures comprises a mixture of tissue, body fluids, and blood. Because of the presence of the blood component, the aspirate usually is dark red in appearance. It has been observed that the color of the aspirate gives no indication of the amount or relative fraction of the aspirate which constitutes bloos from the patient. Thus the appearance of the aspirate provides no information to the surgeon concerning how much blood has been aspirated from the patient, nor any indication when operative or post-operative transfusion is required. Generally the surgical team monitors the vital signs of the patient, and relies on tests such as complete blood count and hematocrit as well as the gross amount of aspirate to determine the advisability of transfusion. These factors may involve delays in time, or may be imprecise indicators of transfusion requirements.

SUMMARY OF THE PRESENT INVENTION

The present invention generally comprises an apparatus for providing surgical aspiration, and for monitoring the net amount and relative composition of the aspirate. A significant feature of the invention is the provision of a real-time readout of the net amount of blood removed from the patient, so that the surgeon can determine the advisability of transfusion for the patient during the surgical procedure. The relative composition readout also provides the surgeon with an immediate indication of the proficiency of tissue removal relative to removal of body fluids, so that surgical technique can be perfected.

The apparatus for surgical aspiration and monitoring of the aspirated fluids includes a sealable aspiration bottle supported by an electronic weighing scale on a base stand. The bottle cap is provided with a pair of tubing connectors adapted to be secured to a negative gage pressure source and to an aspirating surgical instrument. A pair of electrodes extend from the cap into the bottle and are connected to an electronic circuit which measures the impedance of the fluid/tissue aspirate in the bottle. The base stand includes a bottle shield and interconnect isolation means to prevent incident contact with the bottle that might otherwise cause errors in the weighing scale readout.

The invention includes a microprocessor which is connected to receive the impedance and net weight data of the aspirate. The microprocessor is programmed to correlate this data to determine the relative amounts and net weights of fluid and tissue in the aspirate, and to calculate these factors virtually immediately. A visual display screen supported on the base stand is connected to the microprocessor to receive and display the data calculated thereby. In addition, the relative amounts and net weight of fluid and tissue removed from different portions of the patient's body may be displayed separately, so that in some surgical procedures where it is desirable, such as lipectomy, the amount of tissue removed from differing areas can be substantially equalized.

BRIEF DESCRIPTION OF THE DRAWING

FIG. 1 is a perspective view of the apparatus for surgical aspiration and aspirate monitoring of the present invention.

FIG. 2 is a perspective view of the aspirate bottle assembly of the present invention.

FIG. 3 is a perspective view of the bottle cap and electrode assembly of the present invention.

FIG. 4 is an exploded view of the aspirate bottle, electrode, and cap assembly of the present invention.

FIG. 5 is a side elevation of the aspirate bottle cap and cap shield assembly of the present invention.

FIG. 6 is a graphic representation of the relative fluid composition of aspirate material as a function of impedance of the aspirate and net weight of the aspirate.

FIG. 7 is a functional block diagram of the electronic circuitry of the aspirate monitoring portion of the present invention.

DESCRIPTION OF THE PREFERRED EMBODIMENT

The present invention generally comprises an apparatus for providing aspiration for surgical procedures, and for quantitatively and qualitatively assessing the aspirate removed from the surgical site. The apparatus is designed to provide to the surgeon an immediate readout not only of the amount of material removed from a surgical patient, but also the relative amounts of tissue and blood which have been removed.

With regard to FIG. 1, a preferred embodiment of the invention includes a base stand 11 having laterally extending legs 12 supported by ground-engaging casters or rollers 13. The legs 12 define an intermediate space 14 dimensioned to receive a vacuum pump adapted to provide negative gage pressure for vacuum aspiration purposes, as will be explained in the following description. A cantilevered table 17 extends laterally from a medial portion of an upwardly extending column 16. The table 17 supports a vacuum aspiration collection bottle assembly, with associated components thereof secured to adjacent portions of the column. Joined to the upper portion of the column 16 is a visual information display 19, which may comprise a cathode ray tube, liquid crystal display panel, or any equivalent device known in the prior art. A recessed handle 21 in a medial portion of the column 16 permits the apparatus to be moved on the casters 13 to any convenient location for easy access to the bottle assembly 18 and direct visualization of the display 19 by the surgeon or other medical practitioner using the invention.

The collection bottle assembly 18 includes a transparent glass or plastic collection bottle 22 having a capacity in the range of 1000–2000 ml. The bottle is supported on the weighing pan 23 of an electronic scale, the scale comprising any of several commercially available digital scales which are self-zeroing and accurate to approximately ±1 gram. The scale pan 23 is provided with a shallow, dished recess to receive and center the bottom of the bottle on the pan. A cap assembly 26 includes a stopper portion 27 which fits into the opening 29 of the bottle 22 in pressure sealing fashion. A pair of tubular members 28 extend through the stopper 27 to a block 31 joined to the upper surface of the stopper. Within the block 31 the tubular members 28 are each coupled to one of a pair of tubing nipples 32. The tubing nipples together with their associated tubular members provide flow communication through the stopper when the bottle is sealed thereby. Furthermore, the tubing nipples are formed of a electrically conductive substance, such as surgical stainless steel or the like.

The collection bottle assembly (FIGS. 2-5) also includes a pair of electrodes 33 extending downwardly from the stopper portion 27 and disposed at a mutually downwardly diverging angle. The electrodes are formed of a chemically inert conductive metal which is provided with a high intrinsic resiliency factor. In their free state the electrodes diverge as shown in FIG. 4; however, when the electrodes are placed into the collection bottle 22 and the stopper 27 is inserted into the bottle opening 29, the resiliency of the electrodes causes them to impinge upon and conform to diametrically opposed inner surface portions of the bottle 22, as shown in FIG. 2. This arrangement assures that the electrodes maintain a fixed maximum spacing when disposed within the bottle.

With regard to FIG. 3, the upper ends of the electrodes 33 extend through the stopper portion 27 into the block 31. Each electrode of electrically connected to one of the tubing nipples 32, so that each tubing nipple serves not only as a flow conduit to the interior of the collection bottle, but also as an electrical connection to one of the electrodes within the bottle. The assembly further includes a cap 34 provided with flange portions 37 dimensioned to engage the block 31 in snap engaging fashion for quick assembly thereto and removal therefrom, as shown in FIGS. 2, 4 and 5. The cap further includes two pair of resilient electrical contacts 36, each pair disposed to snappingly engage one of the tubing nipples 32 when the cap 34 is secured to the block 31. Each pair of the contacts 36 is connected to one of a pair of conductors in a cable 38 extending from the cap 34 and terminating in a male electrical plug connector 39.

Extending laterally from the column 16 superjacently of the table 17 is a support bracket 41, as shown in FIG. 2. The bracket 41 includes a pair of channels 42 adapted to receive a pair of tubing members 43 extending to and coupled to the tubing nipples 32. The bracket 41 also includes a female plug (not shown) adapted to removably receive the plug connector 39, so that the electrodes 33 may be electrically connected to the electronics within the base stand. A bottle shield 44 is pivotally secured to a portion of the bracket 41, and dimensioned to pivot downwardly to protect the bottle 22 when supported on the scale pan 23. The shield thus protects the bottle from accidental impat or jostling which would otherwise disrupt the weighing process and lead to erroneous results. Furthermore, the shield 44 can be lowered to protect the bottle 22 only when the tubing members 43 are properly secured in the channels 42 and the cap cable 38 is plugged into the receptacle in the bracket 41. A switch (not shown) adjacent to the shield 44 is actuable when the shield is pivotted downwardly to protect the bottle, and this switch is connected to prevent operation of the apparatus unless the shield is lowered completely, as will be explained in the following. Thus the shield serves not only to protect the bottle and prevent weighing errors, but also to assure that the tubing and cable are correctly connected to the bottle.

It may be appreciated that one of the tubes 43 is connected to a vacuum source, also termed a negative gage pressure source, to create a pressure within the bottle substantially less than atmospheric pressure. The other of the tubes 43 is connected to an aspirating surgical instrument, such as a suction tip, catheter, cannula, mechanical surgical cutting instrument, or the like. The extreme low pressure causes fluids and tissue to be aspirated into the bottle, where they accumulate. The electronic scale provides a constantly updated net weight of the collected aspirate, and the electrodes 33 are employed to determine the impedance of the aspirate. The impedance factor correlates very closely with the proportion of fluids and tissue in the aspirate. The data from the scale and the electrodes are fed into a microprocessor-based electronic apparatus which calculates the amount of fluid and the amount of tissue in the collection bottle. These data are then displayed on the visual readout screen 19 to apprise the surgeon of these factors, and to aid in the surgical procedure being performed.

It is well established in medical literature that the electrical impedance of physiologic fluids and tissues are significantly different. The dissolved electrolytes in the physiologic fluids provides substantial conductivity, whereas the lipid membranes of cells are relative insulators and exhibit relatively high impedance. In general, the impedance measured across the electrodes 33 is inversely related to the weight of the aspirate in the bottle, and directly related to the percentage composition of tissue in the aspirate. Likewise, the impedance across the electrodes is inversely related to the percentage composition of physiologica fluids in the aspirate. Generally, speaking, the primary component of the physiologic fluids is blood, with a minor amount of lymphatic fluid and the like in the aspirate.

Given these relationships of impedance to weight, percentage tissue composition, and percentage fluid composition, it is possible to derive equations which precisely describe these relationships. As shown in FIG. 6, these equations may be plotted as a family of curves on a graph of impedance versus weight, each curve representing a percentage of relative fluid composition of the aspirate. Whenever the weight and impedance of the aspirate is known, this graphic representation will define a unique point on the graph, yielding the percentage fluid composition and, by subtraction, the percentage tissue composition. If that unique point does not fall on one of the plotted curves in the family of curves, a simple interpolation algorithm can determine the actual relative composition.

It may be appreciated that the percentage fluid composition and the percentage tissue composition may be determined by a lookup table and an algorithm provided to search the table for the closest data points for weight and resistivity. In the preferred embodiment, however, the microprocessor is programmed to determine the desired information by solving the equations represented by the family of curves in the plot of FIG. 6. This may be accomplished by first solving for the total bottle bulk resistivity in ohm-cm as a function of weight and impedance:

$$\text{RESISTIVITY } K(W) = \text{IMPEDANCE}$$

where K(W) is a function of the weight of the aspirate within the bottle. The percentage composition is then determined as a function of bulk resistivity:

%TISSUE=F(R)

where F(R) is a function of the calculated resistivity. The K and F functions comprise simple algebraic expressions with experimentally determined constants, and are easily derived by those having ordinary skill in the art.

The electronic system for performing the analysis of the aspirate outlined above is shown in block diagram form in FIG. 7. A key component of the system is a single board computer 51, including a programmable microprocessor or the equivalent logic system together with approximately 64k RAM. The board also includes an alphanumeric video display generator which is connected to the video display 19. The computer 51 is connected to a data buss 52, and thence to several peripheral components. For example, the electrodes 33 are connected through the cable 38 and other wiring to an impedance measuring section, which determines the impedance across the electrodes and provides this information in digital form to the buss 52. The electronic scale 54 comprises a digital scale as described previously, and is supported in the table 17. It weighs the contents of the collecting bottle, and transmits this data in digital form through a scale interface 55 to the buss 52. The scale 54 in fact includes its own microprocessor, which zeroes the scale reading the empty bottle weight, together with the tubing, cable, and cap assembly, whenever the system power is first turned on, or whenever the bottle shield is raised (for changing bottles, etc.).

The position of the bottle shield 44 is sensed by a bottle door switch 56 actuated only when the shield is rotated fully downwardly, as explained previously. The state of the door switch 56 is fed through a switch interface 57 to the data buss 52. Also connected to the buss is a read only memory (ROM) 58, which contains the system software. Also, the computer system is provided with a "watchdog" circuit 59 which monitors the operation of the computer 51 every seven seconds. If the computer operation is interrupted, or other electronic fault should occur, the circuit 59 will blank the video display, thus alerting the user to the existence of a fault condition and the need for servicing.

A further feature of the present invention is the provision of left and right switches 61 and 62, respectively positioned directly below the video display, as shown in FIG. 1. The switches 61 and 62 are provided to permit separation of data concerning the amount and relative composition of aspirate removed from bilaterally symmetrical portions of the surgical patient. For example, in a procedure such as lipectomy, in which it is desired to remove substantially equal amounts of tissue from laterally opposed portions of the body, the left switch 61 is actuated before surgery begins on the left body portion, and the right switch 62 is actuated before the procedure commences on the corresponding right side portion. The data relating to these separate body portions is displayed separately on the screen 19 to allow the surgeon to remove generally equal amounts of tissue from both opposed body portions.

The switches 61 and 62 are connected through a switch interface 63 to the data buss 52. The operating program embodied in the ROM 58 directs the microprocessor to interrogate the interface 63, and to separate the aspirate data according to the settings of the switches. The electronic system also includes an isolated power supply, comprising an isolation transformer having a leakage current less than 10 microamperes, coupled to an EMI filter. The output of the filter is connected to power the color video display 19 and the electronic scale 54, and is also used to drive a logic power supply which generates +5 VDC and 9 VAC to power the computer 51 and the system card 65.

To use the apparatus of the present invention, the apparatus is first connected to 115/230 VAC power, the bottle shield 44 is raised, and a clean collection bottle 22 is placed on the scale pan. The bottle is sealed with a cap assembly 26 and connected, as described previously, to a vacuum source and to a surgical aspiration instrument, and the cable plug 39 is plugged into the instrument. The bottle shield is lowered, causing the scale to zero and the video display to zero. As aspirate is drawn into the bottle 22, the net weight and impedance of the aspirate is constantly recalculated, and the relative composition of tissue and fluid is calculated by the microprocessor. This information is displayed immediately as separate left-right pairs of bar graphs on the display 19, with tissue amount shown as yellow bars and fluid amount shown as adjacent red bars.

A significant feature of the invention is that it provides a real-time indication of not only the amount of tissue, but also the volume of fluid removed from the patient. This information is critical in determining the advisability of transfusing the patient, rather than relying on secondary physiological indicators. Furthermore, the immediate readout of relative composition permits the surgeon to optimize the surgical technique, so that the minimal amount of fluid may be removed in relation to a maximal amount of tissue. These features provide information to the surgeon which has been heretofore unavailable, and represent important advances over prior art surgical instrumentation.

We claim:

1. For use with an aspirating surgical instrument, apparatus including means for collecting aspirate from the surgical instrument, means for monitoring the weight of the aspirate as it is collected, means for determining the impedance characteristic of the aspirate as it is collected, means for calculating the relative amounts of tissue and physiological fluid in the aspirate based on the monitored weight and impedance characteristic, and means for displaying the weight and relative amounts of tissue and physiological fluid of the aspirate.

2. The apparatus of claim 1, wherein said means for collecting the aspirate includes a collection bottle having means to connect to a vacuum source and to the aspirating surgical instrument.

3. The apparatus of claim 2, wherein said collection bottle includes an opening, and further including a cap assembly for releasably sealing said opening.

4. The apparatus of claim 3, wherein said cap assembly includes a pair of fluid flow channels extending therethrough, and further including a pair of electrodes extending downwardly from said cap assembly into said bottle and disposed to be immersed in the aspirate.

5. The apparatus of claim 4, further including a pair of tubing nipples extending from said cap assembly and adapted to be connected to tubing members extending to said vacuum source and to said aspirating surgical instrument, said tubing nipples being formed of a conductive material, each of said pair of electrodes being electrically connected to one of said tubing nipples.

6. The apparatus of claim 5, wherein said cap assembly includes a stopper portion received in said bottle opening, and a cap portion removably secured to said stopper portion, said cap portion including electrical contact means for engaging said tubing nipples exteriorly of said stopper portion in electrically conductive fashion.

7. The apparatus of claim 6, further including an electrical cable extending from said electrical contact means to said means for calculating the relative amounts of tissue and physiologic fluid in the aspirate.

8. The apparatus of claim 2, wherein said means for monitoring the weight of the aspirate includes a weighing scale disposed to support said collection bottle.

9. The apparatus of claim 8, wherein said weighing scale includes a scale pan having a central depression therein dimensioned to receive and secure a bottom portion of said collection bottle.

10. The apparatus of claim 1, wherein said means for determining the impedance characteristic of the aspirate includes a pair of electrodes disposed to be in electrical contact with said aspirate.

11. The apparatus of claim 10, wherein said electrodes are disposed at laterally opposed interior portions of said collection bottle.

12. The apparatus of claim 10, wherein said electrodes are disposed at a fixed spacing within said collection bottle.

13. The apparatus of claim 1, wherein said means for calculating the relative amounts of tissue and physiologic fluid includes microprocessor means connected to receive said monitored weight and impedance characteristic information, and programs means for directing said microprocessor means to calculate the relative amounts of tissue and physiological fluid in the aspirate based on the monitored weight and impedance characteristic.

14. The apparatus of claim 13, further including memory means connected to said microprocessor means and adapted to store a lookup table relating a wide range of weight and impedance characteristic data with corresponding relative tissue and physiologic fluid compositions.

15. The apparatus of claim 13, wherein said microprocessor means includes alphanumeric video generator means for driving said means for displaying the weight and relative amounts of tissue and physiologic fluid of the aspirate.

16. The apparatus of claim 13, further including means for segmenting, storing, and displaying the weight and relative amounts of tissue and physiological fluid removed from differing portions of the patient's body.

* * * * *